(12) United States Patent
Makkar et al.

(10) Patent No.: US 8,667,972 B2
(45) Date of Patent: Mar. 11, 2014

(54) METHODS OF PREPARING CUSTOMIZED, NEUROMUSCULAR MOUTHPIECES FOR ENHANCING ATHLETIC PERFORMANCE

(75) Inventors: Anil Kumar Makkar, Truro (CA); Trevor Robert Laingchild, Carlisle (CA); Preston Joseph Dokuchie, Burlington (CA)

(73) Assignee: 3162212 Nova Scotia Limited, Central Onslow (CA)

( * ) Notice: Subject to any disclaimer, the term of this patent is extended or adjusted under 35 U.S.C. 154(b) by 623 days.

(21) Appl. No.: 12/852,879

(22) Filed: Aug. 9, 2010
(Under 37 CFR 1.47)

(65) Prior Publication Data
US 2011/0186055 A1 Aug. 4, 2011

Related U.S. Application Data

(60) Provisional application No. 61/232,169, filed on Aug. 7, 2009.

(51) Int. Cl.
| | | |
|---|---|---|
| A61F 5/37 | (2006.01) | |
| A61F 5/56 | (2006.01) | |
| A61F 13/00 | (2006.01) | |
| A61F 11/00 | (2006.01) | |
| A61C 5/14 | (2006.01) | |
| A61C 3/00 | (2006.01) | |
| A61C 9/00 | (2006.01) | |
| A61B 19/00 | (2006.01) | |
| A61N 1/00 | (2006.01) | |

(52) U.S. Cl.
USPC ........... 128/862; 128/846; 128/848; 128/857; 128/861; 128/898; 433/6; 433/7; 433/18; 433/19; 433/24; 433/214; 607/2; 607/46; 607/47

(58) Field of Classification Search
USPC .......... 128/846, 848, 857, 859–861; 433/6, 7, 433/18, 19, 24, 213, 214; 607/2, 46–47
See application file for complete search history.

(56) References Cited

U.S. PATENT DOCUMENTS

| 2,702,032 A | 2/1955 | Freedland |
| 2,833,278 A | 5/1958 | Ross |

(Continued)

FOREIGN PATENT DOCUMENTS

| EP | 0590208 A2 | 4/1994 |
| GB | 2259649 A | 3/1993 |

(Continued)

OTHER PUBLICATIONS

International Search Report issued Dec. 8, 2010 in respect of corresponding International Application No. PCT/CA2010/001226.

(Continued)

*Primary Examiner* — Patricia Bianco
*Assistant Examiner* — Brandon L Jackson
(74) *Attorney, Agent, or Firm* — Bereskin & Parr LLP/S.E.N.C.R.L., s.r.l.

(57) ABSTRACT

TENS can be applied to the TMJ of an athlete for a period of time to deprogram muscles. After TENS, a desired position of the lower jaw relative to the upper jaw can be determined and recorded. The desired position can be a physiological resting position, or a performance position in which the lower jaw is positioned anteriorly relative to the physiological resting position. A mouthpiece can be prepared including bite portions configured to substantially space apart and position the jaws according to the desired position, and substantially prevent movement of the lower jaw relative to the upper jaw. A connecting portion connects the bite portions within the mouth, and may extend labially along the anterior teeth and associated gum region of the lower jaw, and may be sized and shaped to substantially lie out of the way so as to not impede speech of the athlete.

23 Claims, 11 Drawing Sheets

(56) References Cited

U.S. PATENT DOCUMENTS

| | | | | |
|---|---|---|---|---|
| 3,407,808 | A | 10/1968 | Baldwin | |
| 3,411,501 | A | 11/1968 | Greenberg | |
| 3,457,916 | A | 7/1969 | Wolicki | |
| 3,496,936 | A | 2/1970 | Gores | |
| 3,513,838 | A | 5/1970 | Foderick et al. | |
| 4,114,614 | A | 9/1978 | Kesling | |
| 4,337,765 | A | 7/1982 | Zimmerman | |
| 4,672,959 | A | 6/1987 | May et al. | |
| 4,765,324 | A | 8/1988 | Lake, Jr. | |
| 5,018,533 | A * | 5/1991 | Hawkins | 128/848 |
| 5,082,007 | A | 1/1992 | Adell | |
| 5,152,301 | A | 10/1992 | Kittelson et al. | |
| 5,339,832 | A | 8/1994 | Kittelson et al. | |
| 5,365,946 | A | 11/1994 | McMillan | |
| 5,385,155 | A | 1/1995 | Kittelsen et al. | |
| 5,386,821 | A | 2/1995 | Poterack | |
| 5,406,963 | A | 4/1995 | Adell | |
| 5,490,520 | A | 2/1996 | Schaefer et al. | |
| 5,566,684 | A | 10/1996 | Wagner | |
| 5,584,687 | A | 12/1996 | Sullivan et al. | |
| 5,718,575 | A | 2/1998 | Cross, III | |
| 5,826,581 | A * | 10/1998 | Yoshida | 128/859 |
| 5,865,619 | A | 2/1999 | Cross, III et al. | |
| 5,931,164 | A | 8/1999 | Kiely et al. | |
| 6,012,919 | A | 1/2000 | Cross, III et al. | |
| 6,082,363 | A | 7/2000 | Washburn | |
| 6,092,524 | A | 7/2000 | Barnes, Sr. | |
| 6,109,266 | A | 8/2000 | Turchetti | |
| 6,152,138 | A | 11/2000 | Brown et al. | |
| 6,178,967 | B1 | 1/2001 | Barnes, Sr. | |
| 6,200,133 | B1 | 3/2001 | Kittelsen | |
| 6,237,601 | B1 | 5/2001 | Kittelsen et al. | |
| 6,371,758 | B1 * | 4/2002 | Kittelsen | 433/6 |
| 6,415,794 | B1 | 7/2002 | Kittelsen et al. | |
| 6,491,036 | B2 | 12/2002 | Cook | |
| 6,505,625 | B1 | 1/2003 | Uenishi | |
| 6,505,626 | B2 | 1/2003 | Kittelsen et al. | |
| 6,505,627 | B2 | 1/2003 | Kittelsen et al. | |
| 6,505,628 | B2 | 1/2003 | Kittelsen et al. | |
| 6,508,251 | B2 | 1/2003 | Kittelsen et al. | |
| 6,510,853 | B1 | 1/2003 | Kittelsen et al. | |
| 6,539,943 | B1 | 4/2003 | Kittelsen et al. | |
| 6,553,996 | B2 | 4/2003 | Kittelsen et al. | |
| 6,581,604 | B2 | 6/2003 | Cook | |
| 6,588,430 | B2 | 7/2003 | Kittelsen et al. | |
| 6,598,605 | B1 | 7/2003 | Kittelsen et al. | |
| 6,626,180 | B1 | 9/2003 | Kittelsen et al. | |
| 6,675,806 | B2 | 1/2004 | Kittelsen et al. | |
| 6,675,807 | B2 | 1/2004 | Kittelsen et al. | |
| 6,691,710 | B2 | 2/2004 | Kittelsen et al. | |
| 6,820,623 | B2 | 11/2004 | Cook | |
| 7,299,804 | B2 | 11/2007 | Kittelsen et al. | |
| 7,404,403 | B2 | 7/2008 | Farrell | |
| 7,451,767 | B2 | 11/2008 | Keropian | |
| 2002/0066454 | A1 | 6/2002 | Kittelsen et al. | |
| 2002/0144686 | A1 | 10/2002 | Cook | |
| 2002/0144690 | A1 | 10/2002 | Kittelsen et al. | |
| 2003/0101999 | A1 | 6/2003 | Kittelsen et al. | |
| 2004/0103905 | A1 | 6/2004 | Farrell | |
| 2006/0011204 | A1 | 1/2006 | Maher | |
| 2008/0138766 | A1 | 6/2008 | Jansheski | |
| 2008/0206707 | A1 | 8/2008 | Gelb | |
| 2008/0215113 | A1 * | 9/2008 | Pawlowicz | 607/46 |
| 2009/0020130 | A1 | 1/2009 | Eubank | |

FOREIGN PATENT DOCUMENTS

| | | | |
|---|---|---|---|
| WO | 9806349 | A1 | 2/1998 |
| WO | 2006116177 | A2 | 11/2006 |

OTHER PUBLICATIONS

International Search Report issued Jan. 12, 2011 in respect of related International Application No. PCT/CA2010/001333.

P. Bracco, A. Deregibus, R. Piscetta, Effects of different jaw relations on postural stability in human subjects, Neuroscience Letters, 2004, pp. 228-230, vol. 356.

Shawn M. Arent, Jennifer McKenna, & Devon Golem, Effects of a neuromuscular dentistry-designed mouthguard on muscular endurance and anaerobic power, Comparative Exercise Physiology, 2010.

Arent, S.M., Pellegrino, J., McKenna, J., & Jaouhari, C.A., Effects of a neuromuscular dentistry-designed mouthguard on muscular endurance and anaerobic power, Dept. of Exercise Science & Sport Studies, Rutgers, The State University of New Jersey, New Brunswick, NJ.

Shawn M. Arent, Jennifer McKenna, & Devon Golem, Effects of a neuromuscular-dentistry designed mouthguard on muscular endurance and anaerobic power, Rutgers University Human Performance Laboratory, Department of Exercise Science & Sport Studies, Rutgers, the State University of New Jersey, New Brunswick, NJ.

Materials filed Sep. 19, 2011 in respect of related U.S. Appl. No. 12/871,396.

* cited by examiner

METHODS OF PREPARING CUSTOMIZED, NEUROMUSCULAR MOUTHPIECES FOR ENHANCING ATHLETIC PERFORMANCE

CROSS-REFERENCE TO RELATED APPLICATION

This application claims priority to U.S. Provisional Application No. 61/232,169 filed on Aug. 7, 2009, the entire contents of which are hereby incorporated herein by reference.

FIELD

This specification relates to customized mouthpieces for enhancing athletic performance. This specification also relates to neuromuscular dentistry.

BACKGROUND

The following paragraphs are not an admission that anything discussed in them is prior art or part of the knowledge of persons skilled in the art.

U.S. Pat. No. 6,178,967 to Barnes, Sr. discloses a mouth protector designed to minimize discomfort and speech interference associated with conventional athletic mouthpieces and includes a pair of posterior splints for encompassing the posterior teeth. Each posterior splint includes an inner and outer wall, both of which terminate at or near the gum line so as to minimize discomfort to the wearer. The posterior splints may be interlinked with a connecting strip that is disposed behind the anterior teeth and extends across the wearer's palate. The device is designed to protect either the upper or lower posterior teeth while allowing a wearer's tongue to contact the anterior teeth thereby minimally interfering with clear speech.

United States Patent Publication No. 20080206707 to Gelb discloses oral appliances which reside within the mouth and which bring the lower jaw and/or the tongue forward to increase airway flow during sleep or physical activity. The oral appliances are constructed such that they may be optionally customized to an individual user's mouth shape. Methods of using such oral appliances are also provided.

United States Patent Publication No. 20090020130 to Eubank discloses an oral appliance that includes a first arch adapted to receive at least some of a user's teeth and a second arch adapted to receive at least some of the user's teeth. The first arch includes an anterior substantially planar region. The second arch includes an anterior bearing point that contacts the anterior substantially planar region of the first arch when the user bites down with the oral appliance inserted in the user's mouth and the user's temporomandibular joint in its proper natural position. The oral appliance may be used to help maintain stability of one or more aspects of the user's masticatory system, including at least helping to maintain proper positioning of the user's temporomandibular joint.

INTRODUCTION

In an aspect of this specification, a method of preparing a customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, comprises the steps of: applying transcutaneous electric neural stimulation generally to the temporomandibular joint for a period of time to deprogram muscles associated with the temporomandibular joint; tracking movement of the lower jaw relative to the upper jaw, determining a desired position of the lower jaw relative to the upper jaw, and recording the desired position; and forming the mouthpiece including a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw, and a connecting portion connecting the bite portions within the mouth, the connecting portion extending labially along the anterior teeth and associated gum region of the lower jaw, the connecting portion sized and shaped to substantially lie out of the way so as to not impede speech of the athlete.

In an aspect of this specification, a customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, the lower jaw arrangeable relative to the upper jaw according to a desired position, comprises: a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw; and a connecting portion connecting the bite portions within the mouth, the connecting portion extending labially along the anterior teeth and associated gum region of the lower jaw, the connecting portion sized and shaped to substantially lie out of the way so as to not impede speech of the athlete.

In an aspect of this specification, a method of preparing a customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, comprises the steps of: (a) applying transcutaneous electric neural stimulation generally to the temporomandibular joint; (b) ceasing the transcutaneous electric neural stimulation, and allowing the lower jaw to relax to a resting position; (c) repeating steps (a) and (b) at least two more times to ensure thorough deprogramming of muscles associated with the temporomandibular joint; (d) using electromyography to track movement of the lower jaw relative to the upper jaw, and to determine a desired position of the lower jaw relative to the upper jaw, and recording the desired position; and (e) forming the mouthpiece including a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw, and a connecting portion connecting the bite portions within the mouth.

Other aspects and features of the teachings disclosed herein will become apparent, to those ordinarily skilled in the art, upon review of the following description of the specific examples of the specification.

DRAWINGS

The drawings included herewith are for illustrating various examples of articles, methods, and apparatuses of the present specification and are not intended to limit the scope of what is taught in any way. In the drawings:

FIGS. 8A, 8B and 8C are side, front and top, respectively, of the customized, neuromuscular mouthpiece shown in FIG. 6;

DESCRIPTION OF VARIOUS EMBODIMENTS

Various apparatuses or processes will be described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. The applicants, inventors or owners reserve all rights that they may have in any invention disclosed in an apparatus or process described below that is not claimed in this document, for example the right to claim such an invention in a continuing application and do not intend to abandon, disclaim or dedicate to the public any such invention by its disclosure in this document.

It has been said that the temporomandibular joint (TMJ) is the most complicated joint in the human body. The TMJ is the articulation between the condyle of the mandible and the squamous portion of the temporal bone. The condyles are elliptically shaped with its long axis orientated mediolaterally. The articular surface of the temporal bone is composed of the concave glenoid fossa and the convex articular eminence. The meniscus is a fibrous saddle shaped structure that separates the condyle and the temporal bone. The meniscus and its attachments divide the joint into superior and inferior spaces. When the mouth opens, two distinct motions occur at the joint. The first is rotational around a horizontal axis through the condylar heads. The second is translational; the condyle and meniscus move together anteriorly beneath the eminence. Several muscles control the movement of not only the muscles of the face and jaw but of the TMJ themselves. The proper function and balance of the TMJ is related to the position of the teeth and the movement of muscles controlled by the central nervous system.

The term "neuromuscular", in this case, refers to the science of dentistry. Neuromuscular dentistry is a medical field that seeks to understand the relationships of the TMJs, muscles, teeth and nerves, and focuses on correcting misalignment of the jaw at the TMJ. Neuromuscular dentistry uses instrumentation to measure the patient's jaw movements via computerized mandibular scanning (CMS) or jaw motion analysis (JMA), muscle activity via EMG and TMJ sounds via electro-sonography (ESG) or joint vibration analysis (JVA) to assist in identifying joint derangements. There are various condylar positions within the glenoid fossa, including: the teeth together, the habitual rest position, the physiological resting position, and with mouth opened to the maximum extent. The physiological resting position can be defined as the position of the mandible when at rest, with the condyles in a neutral, unstrained position in the glenoid fossa. Combining both CMS or JMA with low frequency transcutaneous electric neural stimulation (TENS), the neuromuscular dentist is able to locate the physiological resting position and record the relationship between the upper and lower jaw. EMG can be used to measure pre-, mid- and post-treatment conditions before and after TENS.

Once a physiological resting position is determined, the neuromuscular dentist can record a neuromuscular bite registration between the teeth of the lower jaw relative to the teeth of the upper jaw. The neuromuscular bite registration can then be used to prepare a neuromuscular orthotic. The neuromuscular orthotic can be worn by the patient for 3 to 9 months for 24 hours per day to realign the jaw, at which point the several options are available. The orthotic can be continued to be used as an orthopedical realigning appliance. An overlay partial can be made instead of the orthotic. Orthodontic treatment or prosthetic reconstruction of one or both dentitions can occur to discontinue the use of the orthotic.

It has been shown that by using a mouthpiece to maintain the physiological resting position, an athlete can enhance their athletic performance. (See, for example: "Effects of different jaw relations on postural stability in human subjects", P. Bracco, A. Deregibus and R. Piscetta, Neuroscience Letters, Volume 356, Issue 3, 19 Feb. 2004, Pages 228-230; and "Effects of a neuromuscular dentistry designed mouthguard on muscular endurance and anaerobic power", S. M. Arent, J. McKenna and D. L. Golem, Comparative Exercise Physiology, 2010. The entirety of each is hereby incorporated by reference.) In particular, balance, flexibility, range of motion, strength, vertical leap, endurance and/or other physical performance characteristics of an athlete may be enhanced when the lower jaw is in the physiological resting position or near thereto.

Applicant's teachings relate to the use of neuromuscular dentistry techniques to prepare a customized, neuromuscular mouthpiece for the mouth of an athlete. In particular, neuromuscular dentistry can be used to determine a physiological resting position for the athlete. The mouthpiece can be formed according to the physiological resting position, or a performance position that is close to the physiological resting position. The mouthpiece includes a pair of posterior bite pads customized to place the athlete's jaw generally in the desired position. In some examples, the mouthpiece includes a connecting portion that extends labially and is sized and shaped to substantially lie out of the way so as to not impede speech of the athlete.

Figure 1:
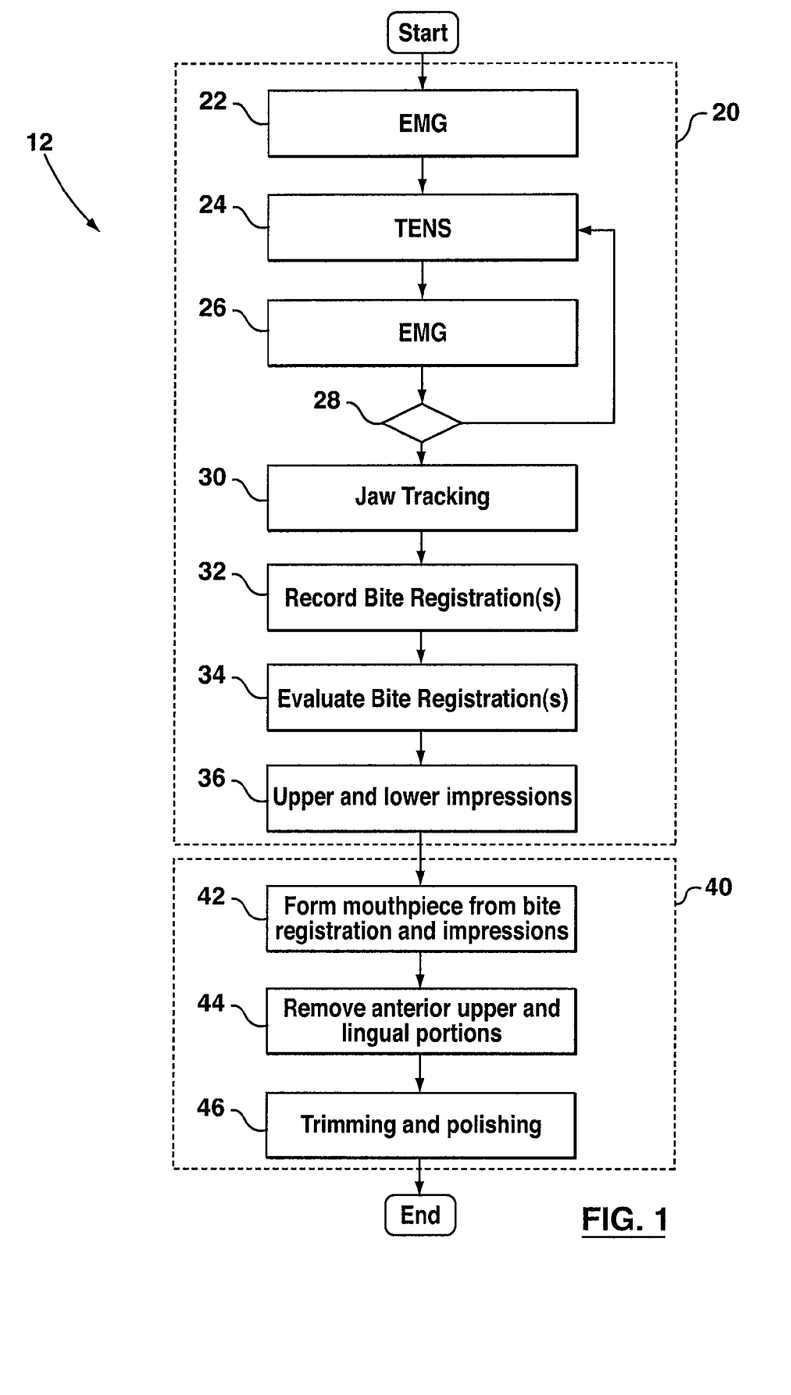
FIG. 1 is a flow chart showing various steps of an example method of preparing a customized, neuromuscular mouthpiece.

Referring to FIG. 1, an example method 12 includes various steps of preparing a customized, neuromuscular mouthpiece. The method 12 can include a primary stage 20 and a secondary stage 40. The primary stage 20 relates to the neuromuscular analysis of the athlete, whereas the secondary stage 40 relates to the preparation of the mouthpiece. In the primary stage 20, a trained neuromuscular dentist, usually in an office or clinic setting, can record at least one neuromuscular bite registration of the athlete. The secondary stage 40 is usually carried out in a laboratory or manufacturing setting, and can be at a separate location from the primary stage 20.

Figure 2A:
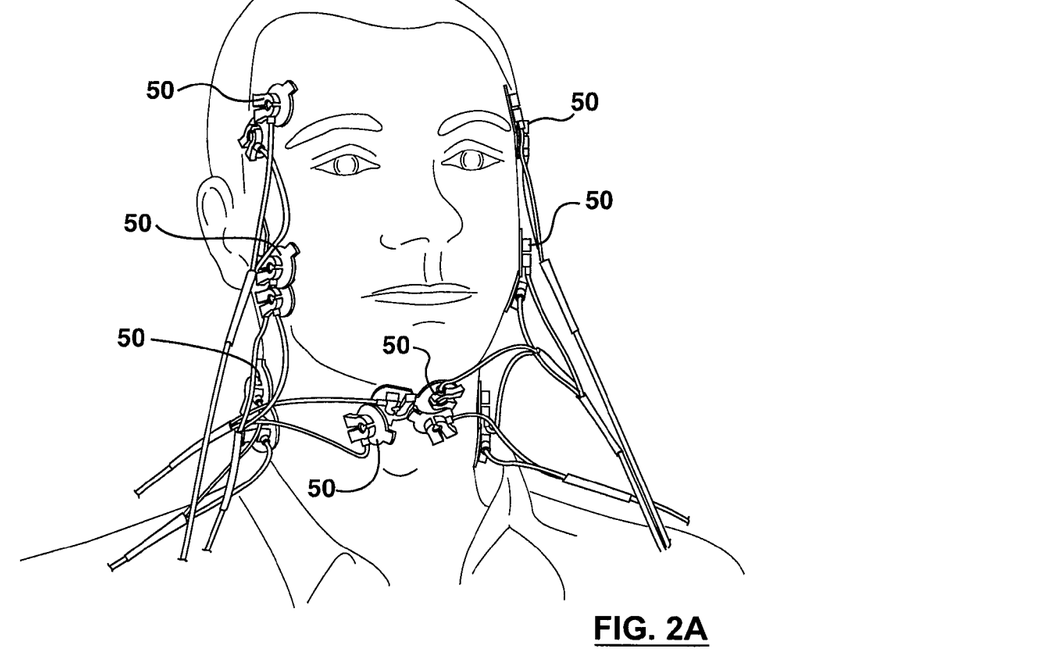
FIG. 2A is a front view of an athlete showing positioning of electrodes for electromyography (EMG)
Figure 3A:
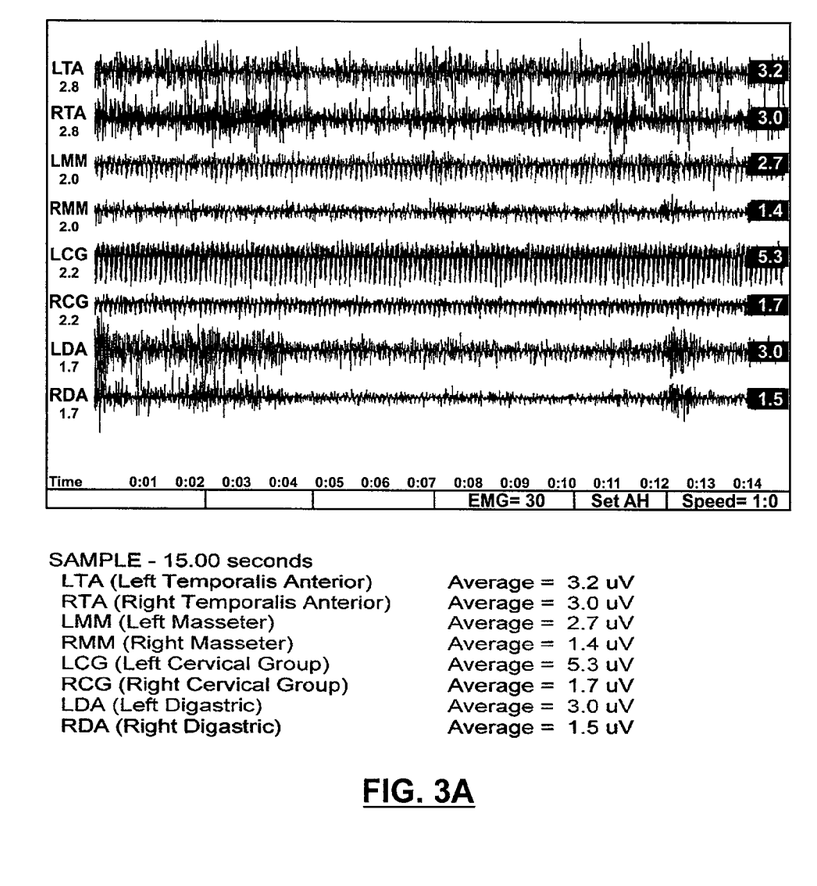
FIGS. 3A and 3B show examples of EMG signals for an athlete before and after TENS, respectively.

Step 22, which is optional, involves the use of an electromyography (EMG). EMG is a technique for evaluating and recording the activation signal of muscles. A K7 EVALUATION SYSTEM™ (Myotronics, Inc., Kent, Wash., U.S.A.) can be used to carry out step 22. DUO-TRODE™ (Myotronics, Inc.) electrodes can be applied to the skin after preparation using 99% isopropyl alcohol. Referring to FIG. 2A, EMG electrodes 50 can be placed at right and left temporalis anterior, right and left masseter, right and left sternocleoid mastoid and right and left digastric positions. FIG. 3A shows an example of a graph of various EMG signals of an athlete at "rest", prior to deprogramming by TENS.

Figure 2B:
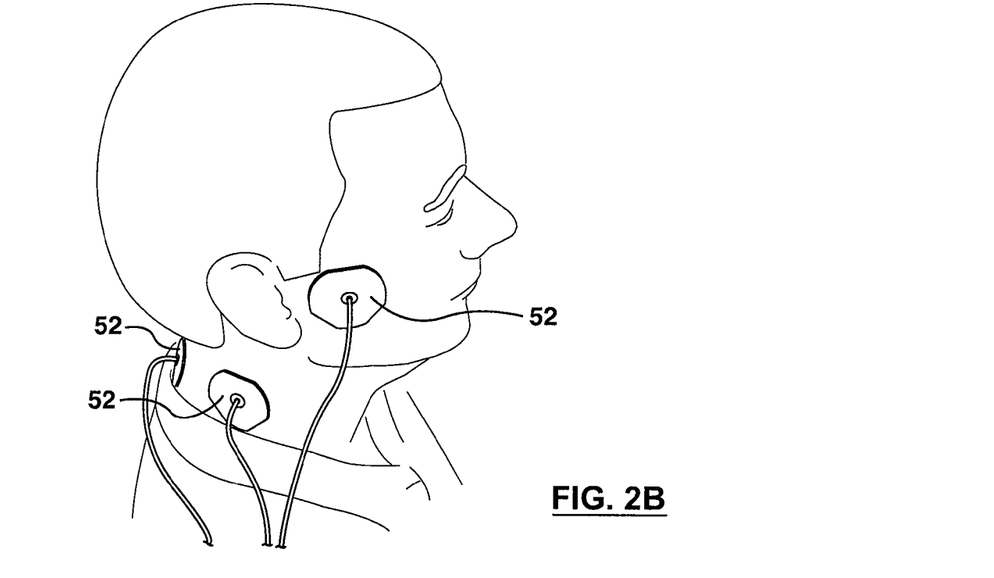
FIG. 2B is a side view of an athlete showing positioning of electrodes for transcutaneous electric neural stimulation (TENS)

In step 24, the athlete is hooked up to an apparatus for TENS. For example, a J4 MYOMONITOR™ or J5 MYOMONITOR™ system (Myotronics, Inc.) can be used. MYOTRODE SG™ (Myotronics, Inc.) electrodes can be applied to the skin after preparation using 99% isopropyl alcohol. Referring to FIG. 2B, TENS electrodes 52 can be placed above cranial nerves V, VII and XI. (The J4 MYOMONITOR™ does not provide for stimulation of cranial nerves XI.)

TENS can be applied anteriorly to the left and right TMJs at the coronoid notch. Low electrical impulse frequency can used to stimulate two nerves specifically, namely, cranial nerve V and cranial nerve VII. Cranial nerve V is otherwise referred to as the trigeminal nerve, and generally controls the mandible and balance. Cranial nerve VII is otherwise referred to as the facial nerve, and generally controls the facial muscle expressions of the face. TENS can be applied for between 45 to 75 minutes to enable thorough deprogramming of the muscles in the face, such as the masseters, anterior temporalis, posterior temporalis, and the digastrics. Deprogramming allows the neuromuscular dentist to determine the physiological resting position.

To promote good results during TENS: the lights can be turned off and sound can be kept to a minimum to avoid distracting the athlete; good posture can be encouraged; and the athlete can be instructed to relax the lower jaw, and allow the lower jaw to hang naturally so that the teeth and lips are not touching. For safety reasons, TENS generally should not to be used on athletes who are pregnant, have a pacemaker, active cancer, temporal arteritis, and/or dermatological skin disorder.

The inventors have discovered that a TENS cycling routine can be used to thoroughly deprogram and break the "engrams" of the facial muscles to allow the physiological resting position (and performance position, as described herein) to be determined. The routine can be carried out as follows. TENS can be applied to the athlete, as described above, but at an increasing amplitude level, while monitoring the athlete using EMG as described above. As the amplitude is steadily increased, the lower jaw is extended outwardly (anteriorly), until the lower teeth contact the upper teeth. Interference in the EMG signals will indicate the point at which the teeth touch. The TENS apparatus may then be set at an amplitude that is slightly less than the "maximum" amplitude that caused the teeth to touch (e.g., 16 milliamps using the J5 MYOMONITOR™ system). For example, the TENS apparatus can be set to 2 milliamps less than the maximum amplitude. The athlete can then be treated for about 10 to 20 seconds. The TENS apparatus may then be shut off to cease stimulation, and the athlete can then be directed to release the lower jaw and allow it to relax to a natural resting position. This cycle may be repeated at least two or more additional times.

Figure 3B:
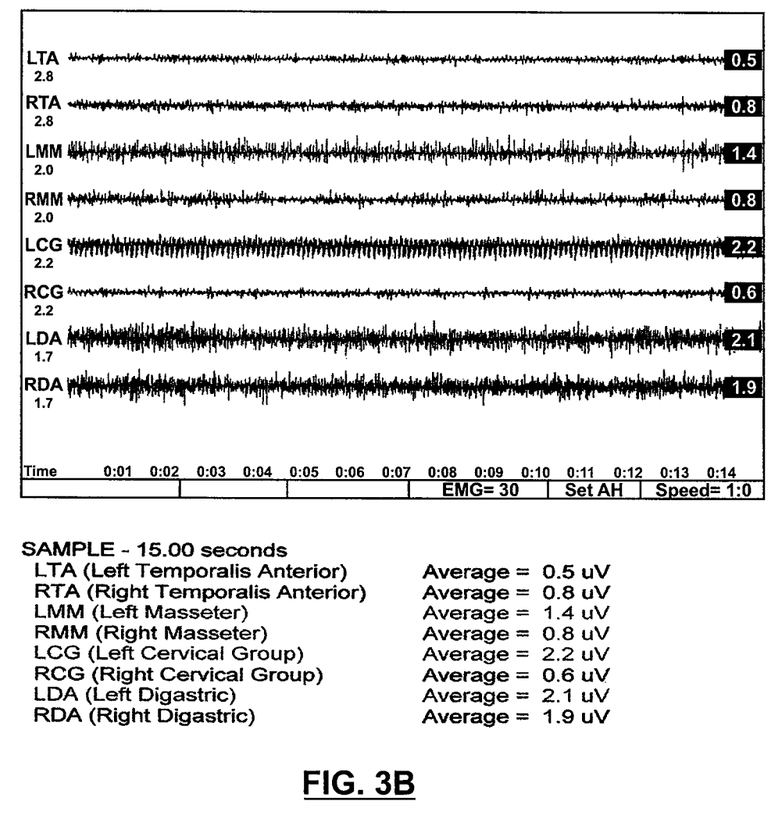

In step 26, which is similar to step 22 and is also optional, EMG can be used to verify a decrease in muscle activation post-TENS. FIG. 3B shows an example of a graph of various EMG signals of the athlete after deprogramming by 60 minutes of TENS. Generally, the muscles are considered to be sufficiently deprogrammed once each reading is 2.0 µV or less. Furthermore, with regards to observing a reduction in muscle activation, it should be appreciated that some of the EMG signals will be more important than others; the left and right digastric signals (denoted LDA and RDA in FIGS. 3A and 3B) are generally considered to be less important than the other signals when assessing the deprogramming carried out in step 24.

In step 28, based on the EMG results provided by step 26, the neuromuscular dentist may choose to subject the athlete to further TENS according to step 24, or continue to step 30.

In step 30, jaw tracking can be carried out to enable the neuromuscular dentist to record at least one neuromuscular bite registration corresponding to a desired position of the lower jaw relative to the upper jaw. Again, a K7 EVALUATION SYSTEM™ (Myotronics, Inc.) can be used to carry out step 30. Using a micrometer, the neuromuscular dentist can take a measurement of the cementoenamel junction of an upper anterior tooth to the cementoenamel junction of a lower anterior tooth (referred to as the Shimbashi measurement), as well as the width of the central incisor measurements to enter into software associated with the K7 EVALUATION SYSTEM™. Using the K7 equipment, recordings are made of the movement of a small, high polarity magnet that is placed along the gum below the lower front teeth. The athlete can be directed between various opening, closing, swallowing and chewing movements, and the jaw positions analyzed. Typically, jaw tracking analysis generates a Scan 4/5, an example of which is provided as FIG. 4. Scan 4/5 provides the data for determining the physiological resting position 54 for the athlete.

The inventors have found that, for the purposes of an athletic mouthpiece, optimal athletic performance is not necessarily obtained by positioning the jaws according to the physiological resting position. For the purposes of recording the neuromuscular bite registration, the desired position of the lower jaw relative to the upper jaw can range from the physiological resting position, to a performance position, in which the lower jaw is positioned anteriorly in relation to the physiological resting position. In some cases, the performance position is located 1.0 to 1.5 mm anteriorly relative to the physiological resting position. In some cases, the performance position is located 0.5 to 1.0 mm anteriorly relative to the physiological resting position. In some cases, the performance position is located 0.0 to 0.5 mm anteriorly relative to the physiological resting position.

Figure 4:
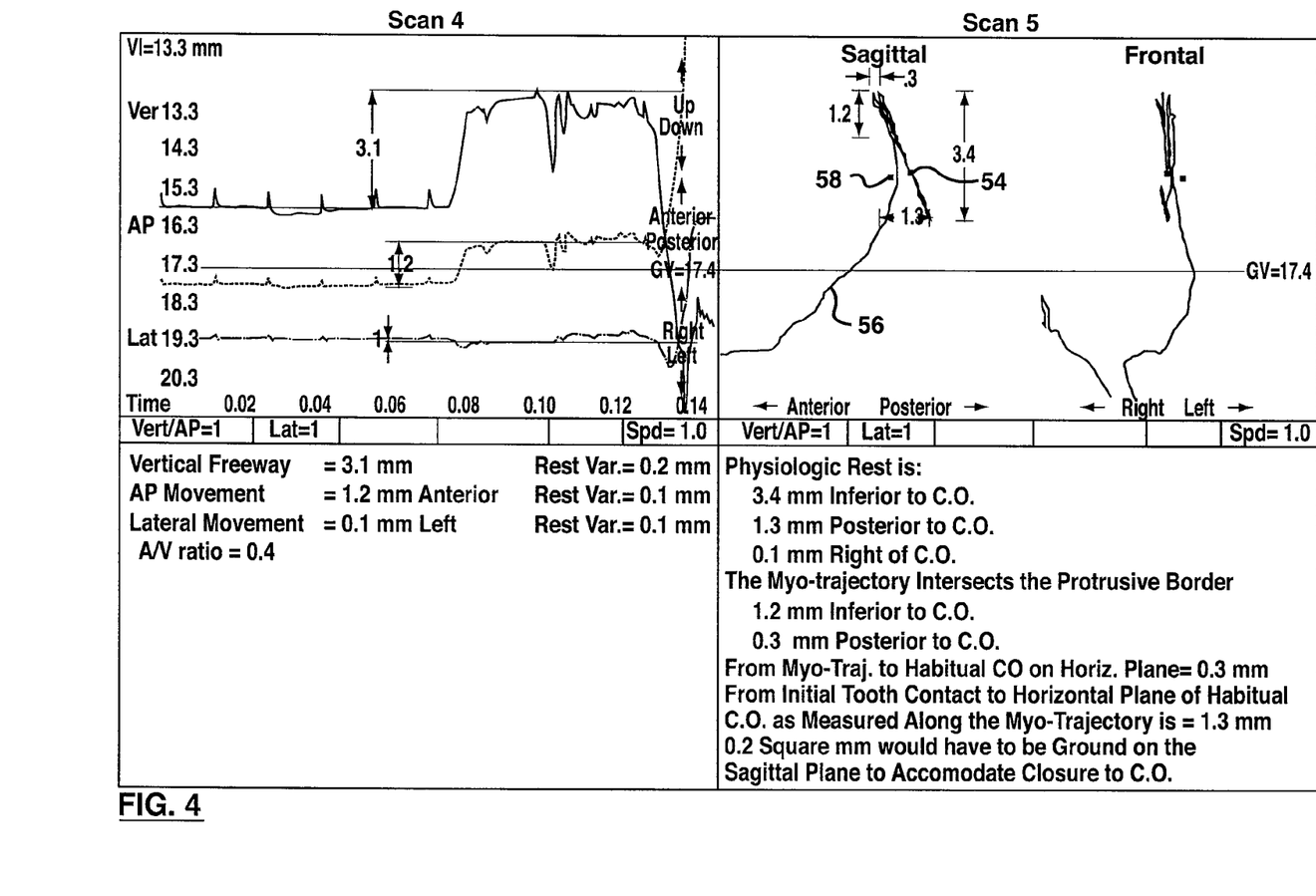
FIG. 4 shows jaw tracking scans for an athlete after TENS.

A routine can be employed to determine the location of the performance position, which is described as follows. The athlete can be instructed to extend the lower jaw outwardly (anteriorly) to the largest extent possible, and hold the lower jaw in the extended position for at least 10 to 20 seconds. The athlete can then be directed to release the lower jaw and allow it to relax to a natural resting position. After maintaining the lower jaw in the extended position, the lower jaw tends not to return to the physiological resting position, but instead releases to a position anteriorly relative to the physiological resting position. The inventors have found that, for many cases, this is a performance position that yields optimum athletic performance. Referring to FIG. 4, the routine is illustrated by line 56, and the performance position is shown at 58.

With reference to the Scan 4 portion of FIG. 4, the inventors have found that, as a general rule, significant enhancement in athletic performance can be obtained if the anterior-posterior amplitude is at least 0.5 mm. Furthermore, to ensure sufficient structural integrity of the mouthpiece, the vertical amplitude should be at least 2.5 mm.

Once the physiological resting position, and optionally the performance position, is determined, the neuromuscular bite registration can be recorded by the neuromuscular dentist in step 32. The neuromuscular dentist may choose to record one, two, three, or more neuromuscular bite registrations. The neuromuscular bite registration material can be injected into the athlete's mouth, and the dentist can monitor position of the lower jaw using the jaw analysis software to ensure that the desired position is maintained over the period of time required for the material to set. A quick set material can be used for recording the neuromuscular bite registration; good results have been obtained using AQUASIL ULTRA MONOPHASE FAST SET™ materials.

If more than one neuromuscular bite registration is recorded in step 32, the neuromuscular dentist can evaluate the different neuromuscular bite registrations in step 34. Generally, the neuromuscular bite registrations can be evaluated by either quantitative or qualitative comparison based on one or more athletic performance characteristics. For example, balance, range of motion, flexibility, and/or strength tests can be carried out to determine which of the neuromuscular bite registrations yields the greatest degree of performance enhancement. The particular neuromuscular bite registration with the best performance can then be selected for forming the mouthpiece.

In step 36, impressions of the upper and lower jaws can be formed. Sufficient impression material should be used so that the entire anatomy including the incisive papilla and hamular notches are included, which will subsequently serve as reference landmarks. Again, good results have been obtained using AQUASIL ULTRA MONOPHASE FAST SET™ materials for the impressions. Also, suitable mold trays may be necessary. Good results have been obtained using the BORDER-LOCK™ tray system. Tray size should be checked for fit with the athlete prior to taking an impression.

Figure 5:
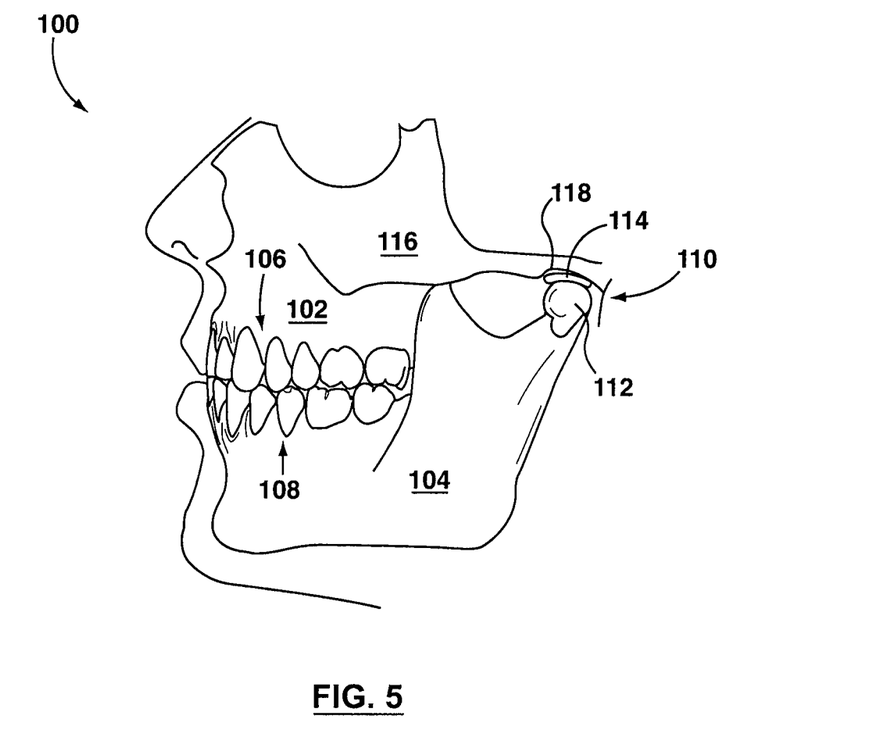
FIG. 5 is a partial profile view of the head of an athlete showing the general location of the teeth, jaws and temporomandibular joint.

Referring now to FIG. 5, a portion 100 of an athlete's head is shown with sections broken away and with muscles, nerves and other tissue omitted to illustrate the upper jaw or maxilla 102 and the lower jaw or mandible 104. The upper jaw 102 includes teeth 106; the lower jaw 104 includes teeth 108. The TMJ 110 movably connects the upper and lower jaws 102, 104 and generally consists of the condyle 112 of the lower jaw 104, the articular disk 114, and the glenoid fossa 118 of the temporal bone 116. The lower jaw 104 is arrangeable relative to the upper jaw 102 according to a physiological resting position, or the performance position, as previously described.

Figure 6:
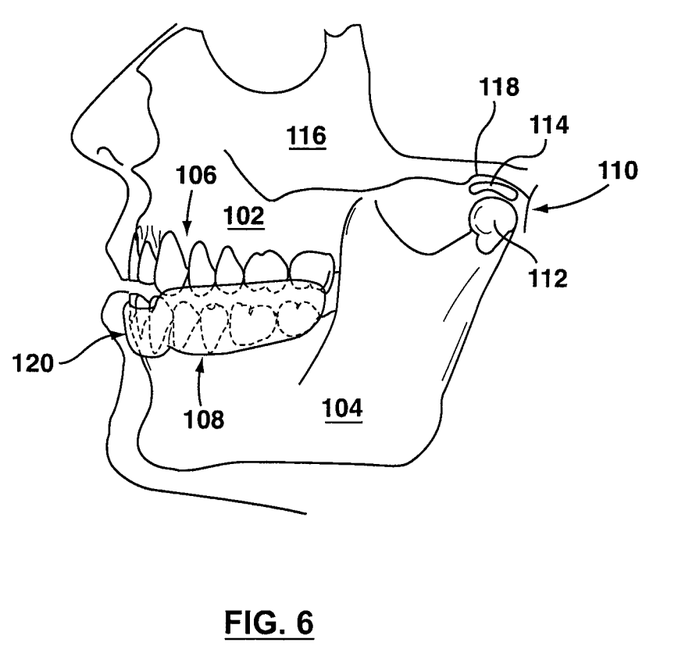
FIG. 6 is a partial profile view of the athlete shown in FIG. 5 wearing a customized, neuromuscular mouthpiece.

FIG. 6 shows the portion 100 of an athlete's head with an example of a customized, neuromuscular mouthpiece 120. The mouthpiece 120 is configured to substantially space apart and position the upper and lower jaws 102, 104 according to the physiological resting position or a performance position that is close to the physiological resting position, and substantially prevent movement of the lower jaw 104 relative to the upper jaw 102.

Unlike other mouthguard designs, the mouthpiece 120 is configured to maintain the lower jaw 104 in a desired position relative to the upper jaw 102 while not substantially impeding speech of the athlete. However, it should be appreciated that the mouthpiece 120 does not provide protection for upper teeth 106, and is considered a non-functioning orthotic, i.e. the athlete cannot eat while wearing the mouthpiece 120. The mouthpiece 120 can be suitable for athletes who are participating in sports in which the risk of impact is relatively low, and verbal communication may be important. For example, the mouthpiece 120 can be suitable for golfers, runners, cyclists, swimmers, tennis players, baseball players, volleyball players, archers, etc.

The mouthpiece 120 is further understood with reference to FIGS. 7A, 7B, 8A, 8B and 8C. The mouthpiece 120 includes a pair of bite portions 122a, 122b. The bite portions 122a, 122b are configured to substantially space apart and position the upper and lower jaws 102, 104 (see FIG. 6) according to the physiological resting position or performance position that is close to the physiological resting position. From the athlete's perspective, the bite portion 122a is configured for the right hand side of the mouth and the bite portion 122b is configured for the left hand side of the mouth. The mouthpiece 120 further includes a connecting portion 124 that connects the bite portions 122a, 122b within the mouth.

Figure 7A:
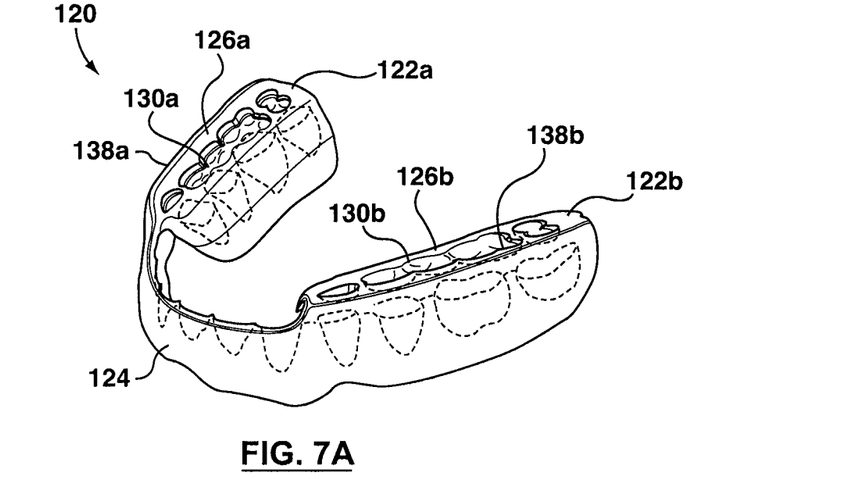
FIGS. 7A and 7B are front, upper, right perspective and rear, lower, left perspective views, respectively, of the customized, neuromuscular mouthpiece shown in FIG. 6.
Figure 7B:
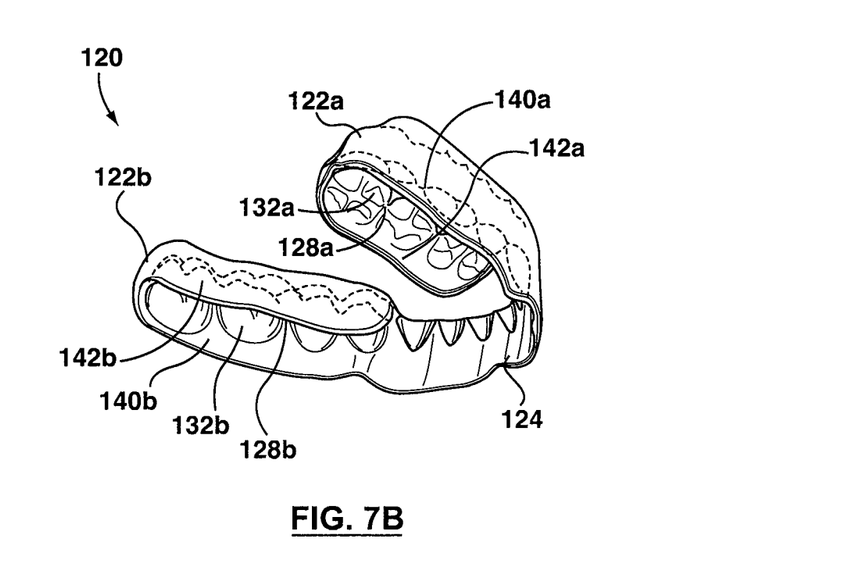

With particular reference to FIGS. 6, 7A and 7B, the bite portion 122a includes an upper engagement surface 126a and a lower engagement surface 128a; the bite portion 122b includes an upper engagement surface 126b and a lower engagement surface 128b. The upper engagement surfaces 126a, 126b face the teeth 106 of the upper jaw 102, and the engagement surfaces 128a, 128b face the teeth 108 of the lower jaw 104. The upper and lower engagement surfaces 126a, 126b, 128a, 128b are configured to engage the upper and lower teeth 106, 108 and substantially prevent movement of the lower jaw 104 relative to the upper jaw 106.

In some examples, the upper engagement surfaces 126a, 126b can include upper indentations 130a, 130b, respectively. The upper indentations 130a, 130b are complementary to at least portions of the teeth 106 of the upper jaw 102. Similarly, the lower engagement surfaces 128a, 128b can include lower indentations 132a, 132b, respectively. The lower indentations 132a, 132b are complementary to at least portions of the teeth 108 of the lower jaw 104.

Figure 9A:
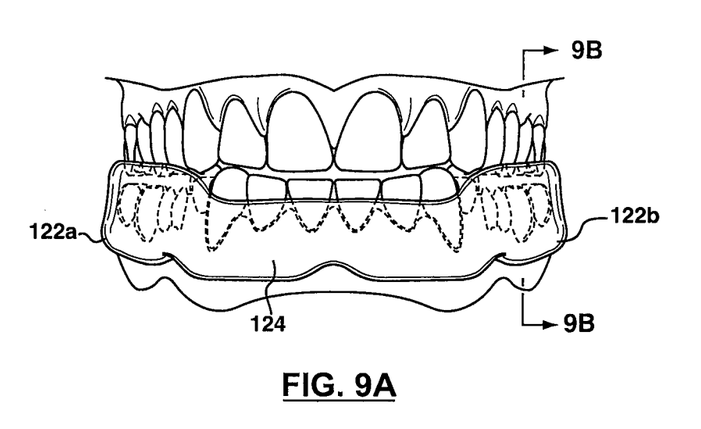
FIGS. 9A and 9B are front and sectional views, respectively, of the athlete and the customized, neuromuscular mouthpiece shown in FIG. 6.

As illustrated in FIG. 9A, the mouthpiece 120 can be configured so that the bite portions 122a, 122b engage the posterior teeth of the upper teeth 106 of the upper jaw 108 and the lower teeth 108 of the lower jaw 104. In other words, the bite portions 122a, 122b can be arranged distally relative to the anterior teeth, whereas the connecting portion 124 can be arranged mesially relative to the posterior teeth.

Using FDI World Dental Federation notation, posterior teeth can be defined as teeth which are numbers 1-8, 1-7, 1-6, 1-5, 1-4, 2-5, 2-6, 2-7, 2-8, and anterior teeth can be teeth which are numbers 1-3, 1-2, 1-1, 2-1, 2-2, 2-3. However, other configurations are possible and within the scope of the applicant's teachings. For example, the bite portions 122a, 122b can only partially engage teeth numbers 1-4, 2-4, 3-4, 4-4, or not engage teeth numbers 1-4, 2-4, 3-4, 4-4 at all. However, generally speaking and depending on the particular athlete, for stability purposes it may be desirable for the bite portions 122a, 122b to at least partially engage teeth numbers 1-8, 1-7, 1-6, 1-5, 2-5, 2-6, 2-7, 2-8, 4-8, 4-7, 4-6, 4-5, 3-5, 3-6, 3-7, 3-8.

In the particular example illustrated, the connecting portion 124 extends labially along the anterior teeth and associated gum region of the teeth 108 of the lower jaw 104. The connecting portion 124 is sized and shaped to substantially lie out of the way so as to not substantially impede speech of the athlete. As illustrated in FIG. 9A, the anterior teeth can be teeth numbers 4-3, 4-2, 4-1, 3-1, 3-2, 3-3. In some examples, the connecting portion 124 can extend from below the gingival line to mid-incisal of the anterior teeth. In other words, the anterior teeth can be exposed from the incisal edge to mid-incisal. The connecting portion 124 can extend about 2 mm below the gingival line at its lowest point, which can be at the mandibular canines (teeth numbers 4-3 and 3-3).

However, it should be appreciated that the size and shape of the connecting portion 124 can vary depending on the athlete and the material selected to form the mouthpiece 120. In other words, dimensions of the connecting portion 124 will vary case by case, and can be selected by considering a balance of strength of the material versus the athlete's tolerance for size. In some examples, the height dimension of the connecting portion 124 can be about 8 mm, and the depth dimension will be about 1 mm (see FIGS. 8B and 8C). In other examples, the height dimension 134 of the connecting portion 124 will be about 6 mm, and the depth dimension 136 will be about 1.5 mm (see FIGS. 8B and 8C).

Furthermore, it will be appreciated that, in other examples in which the mouthpiece is a "lower" oral appliance, the connecting portion may extend lingually along the anterior teeth and associated gum region of the lower jaw and connect the bite portions within the mouth, or the connecting portion may be a combination of both labial and lingual connecting portions. Moreover, in yet other examples, the mouthpieces may take the form of an "upper" mouthguard, in which the connecting portion extends labially along the anterior teeth and associated gum region of the upper jaw and connects the bite portions within the mouth, and optionally with a lingual (i.e. palettal) connecting portion. Accordingly, the teachings herein may not be limited to the preparation of mouthpieces having a connecting portion that extends labially along the anterior teeth and associated gum region of the lower jaw.

Figure 8A:
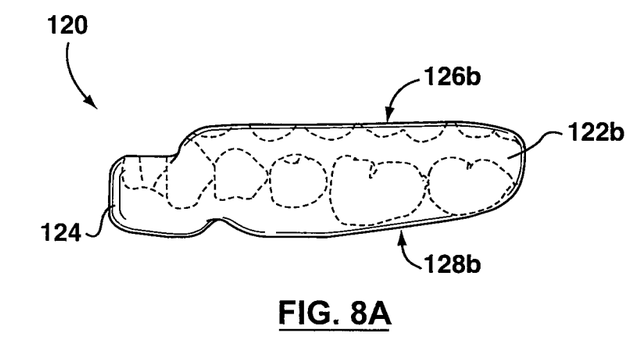
Figure 8B:
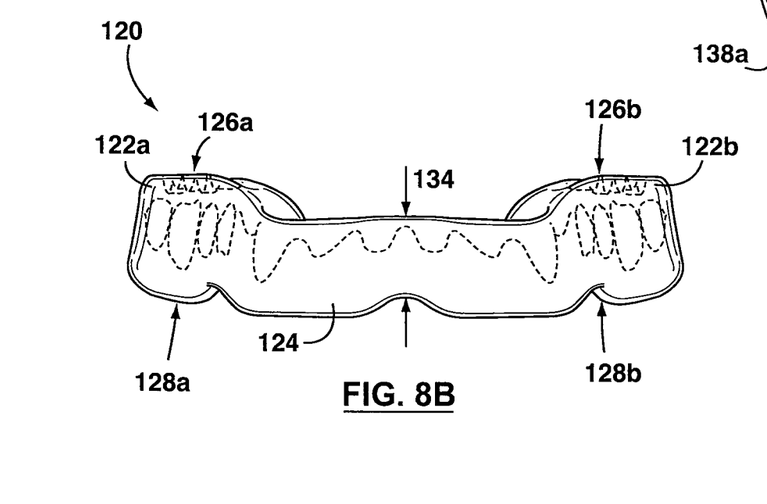
Figure 8C:
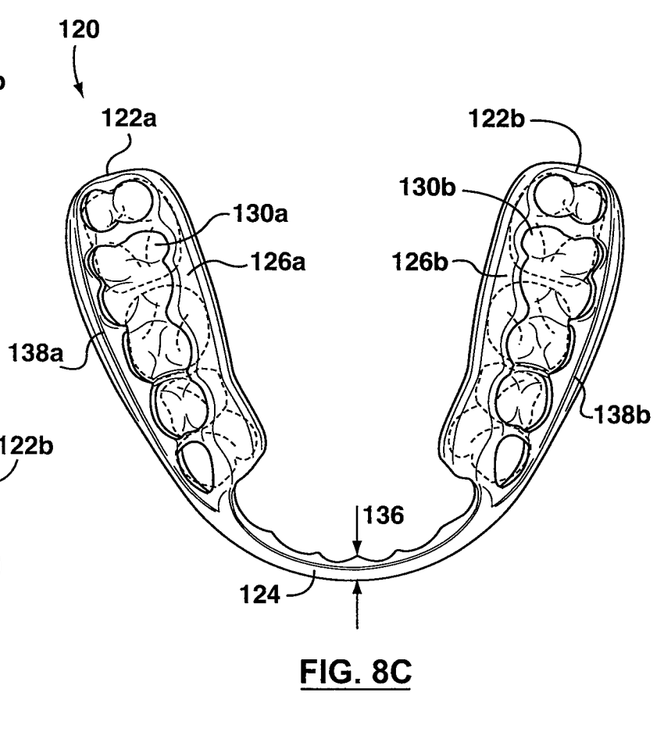
Figure 9B:
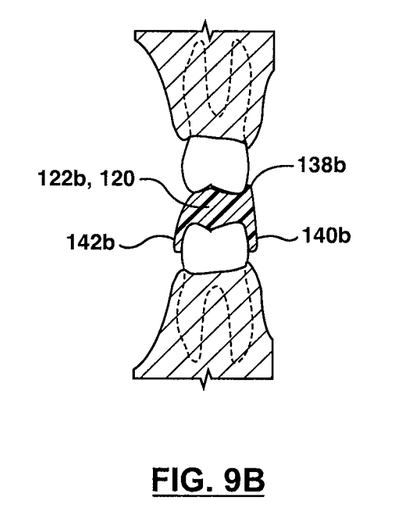

Referring again to the illustrated example, FIG. 9B shows a sectional view of the mouthpiece 120 in engagement with maxillary and mandibular second molars (teeth numbers 2-7 and 3-7). With particular reference to FIGS. 6, 8C and 9B, the upper engagement surfaces 126a, 126b can each further include an upper buccal rail 138a, 138b, respectively. The upper buccal rails 138a, 138b are raised relative to the upper engagement surfaces 126a, 126b and are positioned to engage buccal surfaces of at least a portion of the upper posterior teeth, thereby preventing lateral movement of the lower jaw 104 relative to the upper jaw 102.

Furthermore, with particular reference to FIGS. 6, 7B and 9B, the lower engagement surfaces 128a, 128b can each further include a lower buccal wall 140a, 140b and a lower lingual wall 142a, 142b, respectively. The lower buccal walls 140a, 140b are generally opposing the lower lingual walls 142a, 142b, respectively and are spaced apart to receive at least a portion of the lower posterior teeth therebetween.

Figure 10:
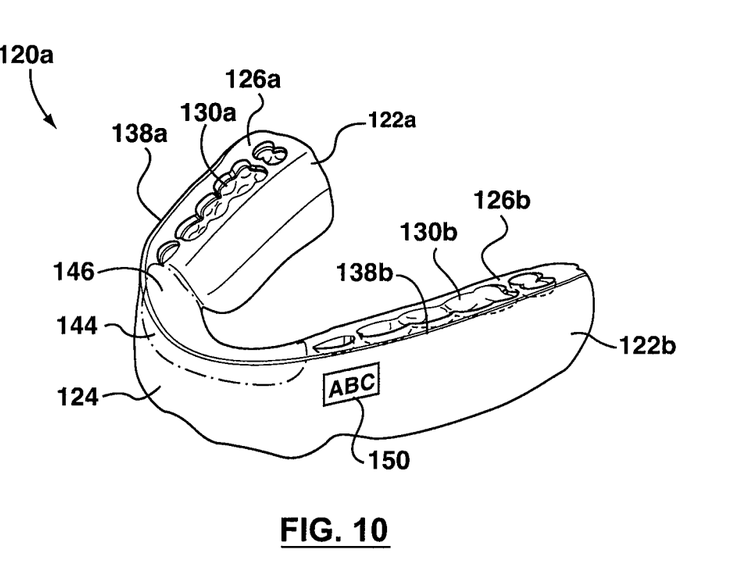
FIG. 10 is a front, upper, perspective view of the customized, neuromuscular mouthpiece shown in FIG. 6, prior to removal of upper and lingual anterior portions.
Figure 11:
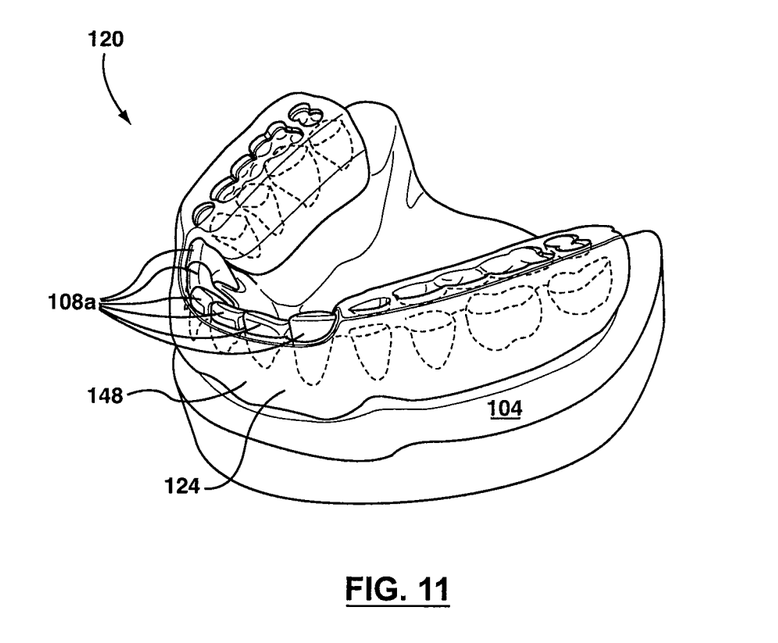
FIG. 11 is a front, upper, perspective view of the customized, neuromuscular mouthpiece shown in FIG. 6 worn by lower teeth of the athlete.

Referring to FIG. 10, the mouthpiece 120 can be initially formed so that it further includes an upper anterior portion 144 and a lingual anterior portion 146. The upper anterior portion 144 and the lingual anterior portion 146 can be removed in a manufacturing step (shown as step 44 in FIG. 1), leaving the connecting portion 124 that extends labially along the anterior teeth 108a and associated gum region 148 of the lower jaw 104 (see FIG. 11).

Furthermore, the mouthpiece 120 can also be formed to include visible indicia 150. For example, the visible indicia 150 can include a corporate logo or the athlete's name.

As described in further detail in the examples below, the mouthpiece 120 can be formed of two or more layers of material bonded to one another. The layers can be of different materials. Assuming at least the outside layer is transparent or translucent, the indicia 150 can be placed between the layers during a forming step. The mouthpiece 120 can be formed of various thermoplastic or acrylic materials, or a combination thereof. Some possibly suitable thermoplastic materials include the materials sold under the brand names TALON™, BITEM™, and ASTRON™. Some possibly suitable acrylic materials include materials sold under the brand names IVO-CAP™, LANG™ GREAT LAKES™, and IMPAK™. The mouthpiece 120 can be formed by manual forming techniques, or by vacuum or pressure forming, or a combination thereof. A suitable pressure forming system is sold under the brand name BIOSTAR™.

Referring back to FIG. 1, the following non-limiting examples of preparing a mouthpiece are provided as illustrative of the second stage 40 of the method 12.

Example 1

In step 42 of FIG. 1, a mouthpiece in accordance with the mouthpiece 120 described above can be formed by first generating upper and lower molds based on the upper and lower impressions taken in step 36 of FIG. 1. The mouthpiece can be formed using the molds and a plurality of laminating and manual forming steps.

In particular, the lower mold can be placed in a BIO-STAR™ pressure forming system, and a 4×125 mm disk of GREAT LAKES™ material can be laminated thereon. After the first laminating step, the lower mold and plastic can be removed from the forming system, and excess material trimmed away. As a second laminating step, a 2×125 mm disk GREAT LAKES™ material can be applied, also using the BIOSTAR™ pressure forming system. Optionally, heat can be manually applied (e.g., using a heat gun) to the first layer before application of the second layer, ensuring good bonding between the layers. After the second laminating step, the lower mold and plastic can be removed from the forming system, and excess material trimmed away. Further laminating steps using the pressure forming system can be carried out. The number of layers and thickness of each layer will vary depending on the desired thickness of the mouthpiece, and in particular the vertical amplitude of the desired position determined at step 30.

The inventors have found that mouthpieces that are formed of two or more layers can be more rigid than mouthpiece that is formed of a single layer. Furthermore, visible indicia can be placed between the laminated plastic layers.

Next, the lower mold with multiple layers of plastic and the upper mold can be installed in an articulator. For example, a STRATOS 100™ or STRATOS 300™ articulator can be used. The upper and lower molds can be fixed in the articulator according to the neuromuscular bite registration selected at step 34. One or more layers of thermoplastic material can then be manually heated and applied to the lower jaw, on top of the laminated plastic, to build the thickness up. The articulator can be closed to capture occlusal indentations of opposing teeth and spacing thereof.

In step 44, anterior upper and lingual portions can be removed, leaving the connecting portion that extends labially along the anterior teeth and associated gum region of the lower jaw. For example, a SCHUTZ™ felt wheel can be used.

In step 46, other trimming can be carried out, using, for example, a felt wheel. An exterior border of appliance can be trimmed to the tissue contours. Other trimming can be done to remove rough edges and excess material. Furthermore, the mouthpiece can be flamed with torch to develop smooth and shiny surface. A buffing step can be carried out using MOLDENT™, and/or a polishing step using KENDA 4-BLUE™.

Use of relatively soft thermoplastic material results in a mouthpiece that may be suitable for athletes participating in sports with a greater possibility of impact, for example, cyclists, tennis players, baseball players, volleyball players, etc.

Example 2

In step 42 of FIG. 1, a mouthpiece in accordance with the mouthpiece 120 described above can be formed by first generating upper and lower molds based on the upper and lower impressions taken in step 36 of FIG. 1. The mouthpiece can be formed using the molds and a plurality of laminating and manual forming steps.

In particular, the lower mold can be placed in a BIOSTAR™ pressure forming system, and a 2.5×125 mm DURASOFT™ material can be laminated thereon. After the laminating step, the lower mold and plastic can be removed from the forming system, and excess material trimmed away. Further laminating steps using the pressure forming system can be carried out. The number of layers and thickness of each layer will vary depending on the desired thickness of the mouthpiece.

Next, the lower mold with plastic and the upper mold can be installed in an articulator. For example, a STRATOS 100™ or STRATOS 300™ articulator can be used. The upper and lower molds can be fixed in the articulator according to the neuromuscular bite registration selected at step 34.

For a second forming step, a suitable acrylic can be mixed. Cold cure and hot cure acrylics are possible, but cold cure is generally easier to work with and more efficient for forming. Good results have been obtained using ORTHO-JET POWDER™. One or more layers of acrylic material can then be manually applied to the lower jaw, on top of the laminated plastic, to build the thickness up. The articulator can be closed to capture occlusal indentations of opposing teeth and spacing thereof. A finishing layer of acrylic can be applied to buccal walls to prevent irregular contours of buccal and lingual aspects.

In step 44, anterior upper and lingual portions can be removed, leaving the connecting portion that extends labially along the anterior teeth and associated gum region of the lower jaw. For example, a SCHUTZ™ felt wheel or a carbide burr can be used.

In step 46, other trimming can be carried out, using, for example, a felt wheel. An exterior border of appliance can be trimmed to the tissue contours. Other trimming can be done to remove rough edges and excess material. Furthermore, the mouthpiece can be pre-polished with pumice. A buffing step can be carried out using MOLDENT™, and/or a polishing step using KENDA 4-BLUE™.

The resulting mouthpiece is formed of a thermoplastic generally on the lower portion (i.e. lower surfaces 128*a*, 128*b* in FIG. 7B) and acrylic generally on the upper portion (i.e. upper surfaces 126*a*, 126*b* in FIG. 7A). Acrylic material results in a mouthpiece that is slightly harder than the thermoplastic-only mouthpiece, and may be suitable for athletes participating in sports with a lesser possibility of impact, for example, golfers, runners, swimmers, archers, etc.

While the above description provides examples of one or more processes or apparatuses, it will be appreciated that other processes or apparatuses may be within the scope of the accompanying claims.

We claim:

1. A method of preparing a customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, the method comprising the steps of:
   applying transcutaneous electric neural stimulation generally to the temporomandibular joint for a period of time to deprogram muscles associated with the temporomandibular joint;
   tracking movement of the lower jaw relative to the upper jaw, determining a desired position of the lower jaw relative to the upper jaw, and recording the desired position; and
   forming the mouthpiece including a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw, and a connecting portion connecting the bite portions within the mouth, the connecting portion extending labially along the anterior teeth and associated gum region of the lower jaw, the connecting portion sized and shaped to substantially lie out of the way so as to not impede speech of the athlete,
   wherein the step of tracking comprises taking at least one neuromuscular bite registration of the athlete while the lower jaw is in the desired position, and
   wherein the step of forming comprises:
      taking impressions of the anterior and posterior teeth of the upper and lower jaw;
      generating upper and lower molds from the impressions;
      mounting the upper and lower molds on an articulator;
      inserting the neuromuscular bite registration in the upper and lower molds to place the upper and lower molds in the desired position;
      removing the neuromuscular bite registration;
      applying material between the upper and lower molds while in the desired position to form the mouthpiece; and
      after the step of applying material, removing upper and lingual anterior portions of the mouthpiece.

2. The method of claim 1, wherein the step of applying material comprises applying a plurality of layers to form the mouthpiece.

3. The method of claim 2, wherein the layers are formed of different materials.

4. The method of claim 3, wherein the upper engagement surfaces are formed at least partially of an acrylic material and the lower engagement surfaces are formed at least partially of a thermoplastic material.

5. The method of claim 2, further comprising placing visible indicia placed between the layers.

6. The method of claim 2, further comprising manually heating a first layer before application of a second layer.

7. The method of claim 1, wherein the desired position is substantially a physiological resting position of the athlete or the lower jaw is positioned up to 1.5 mm anteriorly relative to the physiological resting position.

8. The method of claim 1, wherein the step of tracking comprises taking a plurality of neuromuscular bite registrations of the athlete while the lower jaw is in the desired position, and further comprising evaluating each of the plurality of neuromuscular bite registrations and selecting one of the plurality of neuromuscular bite registrations.

9. The method of claim 1, wherein the step of applying material comprises manual forming, vacuum forming or pressure forming.

10. The method of claim 1, further comprising, before and after the step of tracking, using electromyography to evaluate muscle activation at the temporomandibular joint.

11. The method of claim 1, wherein the period of time is 45 to 75 minutes.

12. The method of claim 1, wherein the transcutaneous electric neural stimulation is applied generally to a cranial nerve V and a cranial nerve VII of the athlete.

13. A customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, the lower jaw arrangeable relative to the upper jaw according to a desired position, the mouthpiece comprising:
a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw; and
a connecting portion connecting the bite portions within the mouth, the connecting portion extending labially along the anterior teeth and associated gum region of the lower jaw, the connecting portion sized and shaped to substantially lie out of the way so as to not impede speech of the athlete,
wherein the upper engagement surfaces include upper indentations complementary to at least portions of the posterior teeth of the upper jaw, and
wherein each of the bite portions is formed of at least two layers of material bonded to one another, and further comprising visible indicia disposed between the two layers.

14. The mouthpiece of claim 13, wherein the lower engagement surfaces include lower indentations complementary to at least portions of the posterior teeth of the lower jaw.

15. The mouthpiece of claim 14, wherein the upper engagement surfaces further comprise an upper buccal rail positioned to engage buccal surfaces of at least a portion of the upper posterior teeth.

16. The mouthpiece of claim 15, wherein the lower engagement surfaces further comprise generally opposing lower buccal and lingual walls positioned spaced apart and configured to receive at least a portion of the lower posterior teeth therebetween.

17. The mouthpiece of claim 13, wherein the at least two layers are formed of different materials.

18. The mouthpiece of claim 17, wherein the upper engagement surfaces are formed at least partially of an acrylic material.

19. The mouthpiece of claim 18, wherein the lower engagement surfaces are formed at least partially of a thermoplastic material.

20. A method of preparing a customized, neuromuscular mouthpiece for an athlete, the athlete having a mouth, an upper jaw with anterior and posterior teeth, a lower jaw with anterior and posterior teeth, and a temporomandibular joint movably connecting the upper and lower jaws, the method comprising the steps of:
a) applying transcutaneous electric neural stimulation generally to the temporomandibular joint;
b) ceasing the transcutaneous electric neural stimulation, and allowing the lower jaw to relax to a resting position;
c) repeating steps (a) and (b) at least two more times to ensure thorough deprogramming of muscles associated with the temporomandibular joint;
d) using electromyography to track movement of the lower jaw relative to the upper jaw, and to determine a desired position of the lower jaw relative to the upper jaw, and recording the desired position; and
e) forming the mouthpiece including a pair of bite portions configured to substantially space apart and position the lower jaw relative to the upper jaw according to the desired position, each of the bite portions including an upper engagement surface facing the posterior teeth of the upper jaw and a lower engagement surface facing the posterior teeth of the lower jaw, the upper and lower engagement surfaces configured to engage the upper and lower posterior teeth, respectively, and substantially prevent movement of the lower jaw relative to the upper jaw, and a connecting portion connecting the bite portions within the mouth,
wherein, in step (a), the transcutaneous electric neural stimulation is applied at an amplitude that is slightly less than an amplitude that would cause the teeth of the upper and lower jaws to contact.

21. The method of claim 20, wherein the amplitude at which the transcutaneous electric neural stimulation is applied is determined by using electromyography to track movement of the lower jaw relative to the upper jaw, and increasing the transcutaneous electric neural stimulation until the teeth of the upper and lower jaws contact.

22. The method of claim 21, wherein, in step (a), the transcutaneous electric neural stimulation is applied for about 10 to 20 seconds.

23. The method of claim 20, wherein the desired position is a performance position in which the lower jaw is positioned between about 0.5 and 1.5 mm anteriorly relative to a physiological resting position of the athlete.

* * * * *